United States Patent
Walker et al.

(10) Patent No.: US 7,739,124 B1
(45) Date of Patent: Jun. 15, 2010

(54) SYSTEM, METHOD AND APPARATUS FOR ENCOURAGING THE UNDERTAKING OF A PREVENTATIVE TREATMENT

(75) Inventors: Jay S. Walker, Ridgefield, CT (US); James A. Jorasch, Stamford, CT (US); Geoffrey M. Gelman, Stamford, CT (US); Russell Pratt Sammon, Stamford, CT (US); Andrew P. Golden, Stamford, CT (US); Stephen C. Tulley, Stamford, CT (US); Brian M. Dugan, Tarrytown, CT (US); Timothy A. Palmer, Stamford, CT (US); Terry E. Mayfield, Norwalk, CT (US); John B. Dickerson, New Canaan, CT (US); Michiko Kobayashi, Stamford, CT (US)

(73) Assignee: Walker Digital, LLC, Stamford, CT (US)

( * ) Notice: Subject to any disclaimer, the term of this patent is extended or adjusted under 35 U.S.C. 154(b) by 1770 days.

(21) Appl. No.: 09/678,117

(22) Filed: Oct. 2, 2000

Related U.S. Application Data

(60) Provisional application No. 60/208,752, filed on Jun. 2, 2000.

(51) Int. Cl.
*G06Q 10/00* (2006.01)
(52) U.S. Cl. .................. 705/2; 705/3; 705/4; 705/14
(58) Field of Classification Search .............. 705/2–4
See application file for complete search history.

(56) References Cited

U.S. PATENT DOCUMENTS 4,712,562 A  12/1987  Ohayon et al. .............. 128/672

(Continued)

FOREIGN PATENT DOCUMENTS

WO   WO 97/28445   8/1997

(Continued)

OTHER PUBLICATIONS

Buchanan, Eugene "Health, Not Economics, Fueling Denver Area No-Smoking Policies"; Mar. 5, 1990; vol. 41; No. 24; Sec 1; p. 20; The Denver Business Journal.

(Continued)

*Primary Examiner*—Vanel Frenel
(74) *Attorney, Agent, or Firm*—Fincham Downs, LLC

(57) ABSTRACT

A system and method is disclosed whereby a customer involved in a transaction is offered a benefit to be applied to the transaction in exchange for undertaking or agreeing to undertake some form of preventative treatment. The transaction may be a purchase of goods or services occurring, for example, over the Internet. In one embodiment, the customer may select an option whereby a third party, such as an insurer of the customer, will provide payment for at least part of the transaction, in exchange for the customer undergoing a preventative treatment. The preventative treatment may include a health treatment screening or test. The payment provided may be determined from an expected future savings in insuring the customer if the preventative treatment is undertaken. Payment may also be conditioned upon the customer's agreement to continue his or her insurance coverage with the insurer or to confirm that the preventative treatment was performed. In certain embodiments, the insurer may place a hold against a financial account for the value of the benefit until administration of the preventative treatment is confirmed.

97 Claims, 10 Drawing Sheets

| PREVENTATIVE TREATMENT IDENTIFIER 56 | DESCRIPTION OF PREVENTATIVE TREATMENT 57 | COST 58 | FIRST RESULT OF PREVENTATIVE TREATMENT 59 | SECOND RESULT OF PREVENTATIVE TREATMENT 60 |
|---|---|---|---|---|
| PC-1-0982345 | DENTAL CLEANING | $80 | REDUCE RISK OF CAVITIES BY 40% | REDUCE RISK OF GUM DISEASE BY 20% |
| PC-2-0982345 | MAMMOGRAM | $75 | REDUCE COST OF BREAST CANCER TREATMENT BY 10% | N/A |
| PC-3-0982345 | BLOOD PRESSURE MEASUREMENT & MEDICATION | $50 | RISK OF HEART ATTACK REDUCED TO 10% | INCREASE RISK OF STROKE BY 0.01% |
| PC-4-0982345 | HIV TEST | $10 | REDUCE COST OF HIV TREATMENT BY 30% | N/A |
| PC-5-0982345 | QUIT SMOKING | N/A | REDUCE RISK OF LUNG CANCER BY 80% | REDUCE RISK OF HEART DISEASE BY 20% |
| PC-6-0982345 | PSYCHIATRIC EVALUATION | $50 | RISK OF DEPRESSION REDUCED TO 5% | N/A |
| PC-7-0982345 | EXERCISE 3 TIMES PER WEEK | N/A | REDUCE RISK OF HEART DISEASE BY 30% | RISK OF OSTEOPOROSIS REDUCED TO 10% |
| PC-8-0982345 | EYE EXAM | $30 | REDUCE COST OF EYEGLASSES BY 20% | N/A |

U.S. PATENT DOCUMENTS

| | | | | |
|---|---|---|---|---|
| 4,831,242 | A | | 5/1989 | Englehardt et al. .......... 235/382 |
| 5,018,067 | A | | 5/1991 | Mohlenbrock et al. . 364/413.02 |
| 5,207,580 | A | | 5/1993 | Strecher ..................... 434/238 |
| 5,301,105 | A | * | 4/1994 | Cummings, Jr. ................ 705/2 |
| 5,410,471 | A | | 4/1995 | Alyfuku et al. ........ 364/413.02 |
| 5,473,537 | A | | 12/1995 | Glazer et al. ............. 364/419.2 |
| 5,492,117 | A | | 2/1996 | Eisenberg et al. ........... 128/630 |
| 5,591,104 | A | * | 1/1997 | Andrus et al. ................... 482/7 |
| 5,692,501 | A | | 12/1997 | Minturn ...................... 128/630 |
| 5,722,418 | A | * | 3/1998 | Bro ............................. 600/545 |
| 5,813,863 | A | | 9/1998 | Sloane et al. ............... 434/236 |
| 5,864,822 | A | | 1/1999 | Baker, III .................... 705/14 |
| 5,877,707 | A | | 3/1999 | Kowalick ................... 340/988 |
| 5,937,387 | A | | 8/1999 | Summerell et al. ............. 705/2 |
| 5,953,704 | A | | 9/1999 | McIlroy et al. ................. 705/2 |
| 5,956,689 | A | | 9/1999 | Everhart, III .................. 705/3 |
| 5,967,789 | A | | 10/1999 | Segel et al. ................. 434/236 |
| 6,014,632 | A | * | 1/2000 | Gamble et al. ................. 705/4 |
| 6,039,688 | A | | 3/2000 | Douglas et al. ............. 600/300 |
| 6,061,657 | A | | 5/2000 | Whiting-O'Keefe ........... 705/2 |
| 6,067,522 | A | | 5/2000 | Warady et al. ................. 705/2 |
| 6,067,523 | A | | 5/2000 | Bair et al. ...................... 705/3 |
| 6,077,193 | A | * | 6/2000 | Buhler et al. .................. 482/8 |
| 6,210,272 | B1 | * | 4/2001 | Brown .......................... 463/1 |
| 7,305,347 | B1 | * | 12/2007 | Joao .............................. 705/1 |
| 2002/0049617 | A1 | * | 4/2002 | Lencki et al. .................. 705/4 |
| 2003/0046116 | A1 | * | 3/2003 | Horowitz et al. ............... 705/4 |
| 2005/0187797 | A1 | * | 8/2005 | Johnson ......................... 705/3 |

FOREIGN PATENT DOCUMENTS

WO        WO 00/04512       1/2000

OTHER PUBLICATIONS

"Insurance Commissioner David N. Levinson to Address National Health Insurance Conference"; Sep. 10, 1991; State and Regional News; PR Newswire.

Austin Barra, Judith "Coats' Medical Savings Plan is Part of GOP Health Proposal"; Oct. 13, 1993; Gannett News Service.

Mason, Julie Cohen "The Cost of Wellness; The Evidence is Trickling in: Worksite Wellness Programs Not Only Help Improve Employee's Health, But Also Have a Positive Impact on the Bottom Line."; Jul. 1994; vol. 83; No. 7; p. 29: ISSN: 0025-1895; Management Review.

"Health Insurance Portability and Accountability Act of 1996", Public Law 104-191-104th Congress; Aug. 21, 1996.

"Part-Time, Contingent Worker Benefits: Being Creative Doesn't Mean Being Expensive"; Jun. 1997; vol. 51, No. 12; p. 37-40; ISSN: 0013-6808; Coden: EBPVAL; Employee Benefit Plan Review.

"Cigarette Smoking Among Adults-United States, 1995"; Dec. 26, 1997; No. 51; vol. 46; p. 1217; ISSN: 0149-2195; Morbidity and Mortality Weekly Report.

"Fiscal Fitness" How Wellness Programs Can Boost the Bottom Line; Jul. 1998; No. 7, vol. 42; p. 17; ISSN: 0273-7930; Indiana Business Magazine.

Brotherton Phaedra "Paybacks Are Healthy; Human Resource Benefits; Focus on HR Benefits"; No. 9, vol. 43; p. S2; ISSN: 1047-3149; HRMagazine.

Peterson Wolff, Maggie "Incentives Drive Employee Wellness Program"; Oct. 1998; vol. 9; No. 12; p. 22; Quad-State Business Journal.

Kalbfleisch, Robin "Healthy Rewards: From Weekend Getaways to Each Rewards, Incentive-Based Wellness Programs Can Help Employees Get More Bang for Their Benefits Buck"; Nov. 1998; v. 22 (10) N'98 p. 19; ISSN: 0703-7732.

Asp, Karen "Prevention First: Consider Occupational Health Services to Help Prevent Workplace Injuries", Jan. 1999, vol. 43; No. 1; p. 20; Indiana Business Magazine.

Newman, Berry "Penalties, Incentives and Wellness Programs After HIPAA"; Mar. 1999; vol. 24; No. 1; p. 29-32; ISSN: 0361-4050; Coden: CMPWAB; Employee Benefits Journal.

Dunham, Sharon "Rewards for Good Health; Company Offers Employee A Monetary Incentive to Keep in Shape"; May 1, 1999; p. 01C; The Bismarck Tribune.

"Department of Health and Human Resources, Federal Register Part VI"; Aug. 20, 1999.

Bonn, Dorothy "Genetic Testing and Insurance: Fears Unfounded?"; ISSN: 0099-5355 Apr. 29, 2000; The Lancet.

Powell, Don R "Characteristics of Successful Wellness Programs"; Sep. 1999; vol. 24, No. 3, p. 15-21; ISSN: 0361-4050; Coden: CMPWAB; Employee Benefits Journal.

"Cash-For-Sterilization: Will It Come to New England?"; Sep. 9, 1999; Medical Ethics; American Health Line.

"Cancer Expense Insurance Policy"; (http://www.af-group.com); download date, May 15, 2000.

"HMOS: Phone Support Programs Helping Them Snuff Out Smoking"; Mar. 31, 2000; vol. 14, No. 10; p. 19; ISSN: 08951551; San Antonio Business Journal.

Lore, Diane "Healthy Living the Painful Truth About Men and Doctors: Macho Attitudes Still Keep Them Away, but Wives, Buddies Can Raise Awareness"; Apr. 4, 2000; Features; p. 1D; The Atlanta Journal and Constitution.

"Merck-Medco Rx Plan Offers Consumers Cash Back on 42 Selected Drugs"; Apr. 20, 2000; vol. 12; Issue 75; Health News Daily.

"CBLO News Briefs"; May 2000; p. 8; Compensation & Benefits for Law Offices.

\* cited by examiner

| CUSTOMER IDENTIFIER 50 | CUSTOMER NAME 51 | AGE 52 | SMOKER? 53 | DRINKER? 54 | HISTORY OF HEART DISEASE 55 |
|---|---|---|---|---|---|
| U-1-923407 | JENIFER JAMES | 45 | NO | YES | NO |
| U-2-923407 | MICHAEL SMITH | 54 | YES | YES | YES |
| U-3-923407 | DAVID STONE | 41 | YES | NO | YES |
| U-4-923407 | SUSAN PETERS | 35 | NO | NO | YES |
| U-5-923407 | KEVIN WRIGHT | 23 | YES | YES | NO |

FIG. 3

| PREVENTATIVE TREATMENT IDENTIFIER 56 | DESCRIPTION OF PREVENTATIVE TREATMENT 57 | COST 58 | FIRST RESULT OF PREVENTATIVE TREATMENT 59 | SECOND RESULT OF PREVENTATIVE TREATMENT 60 |
|---|---|---|---|---|
| PC-1-0982345 | DENTAL CLEANING | $80 | REDUCE RISK OF CAVITIES BY 40% | REDUCE RISK OF GUM DISEASE BY 20% |
| PC-2-0982345 | MAMMOGRAM | $75 | REDUCE COST OF BREAST CANCER TREATMENT BY 10% | N/A |
| PC-3-0982345 | BLOOD PRESSURE MEASUREMENT & MEDICATION | $50 | RISK OF HEART ATTACK REDUCED TO 10% | INCREASE RISK OF STROKE BY 0.01% |
| PC-4-0982345 | HIV TEST | $10 | REDUCE COST OF HIV TREATMENT BY 30% | N/A |
| PC-5-0982345 | QUIT SMOKING | N/A | REDUCE RISK OF LUNG CANCER BY 80% | REDUCE RISK OF HEART DISEASE BY 20% |
| PC-6-0982345 | PSYCHIATRIC EVALUATION | $50 | RISK OF DEPRESSION REDUCED TO 5% | N/A |
| PC-7-0982345 | EXERCISE 3 TIMES PER WEEK | N/A | REDUCE RISK OF HEART DISEASE BY 30% | RISK OF OSTEOPOROSIS REDUCED TO 10% |
| PC-8-0982345 | EYE EXAM | $30 | REDUCE COST OF EYEGLASSES BY 20% | N/A |

| EXPECTED FUTURE COST FOR CUSTOMER U-2-923407 | | | |
|---|---|---|---|
| COST OF FUTURE TREATMENT 61 | PRESENT VALUE OF FUTURE TREATMENT 62 | PROBABILITY THAT FUTURE TREATMENT WILL BE NECESSARY 63 | EXPECTED PRESENT VALUE OF COST OF FUTURE TREATMENT 64 |
| EMS AND AMBULANCE FOR HEART ATTACK | $2050.00 | 20% | $410.00 |
| OPEN HEART SURGERY | $4160.00 | 10% | $416.00 |
| SURGERY FOR BREAST CANCER | $1985.00 | 0.3% | $6.00 |
| CHEMOTHERAPY FOR LUNG CANCER | $1645.00 | 20% | $329.00 |
| FILL A DENTAL CAVITY | $320.00 | 15% | $48.00 |
| EYEGLASSES | $100.00 | 30% | $30.00 |

| OVERALL EXPECTED COST OF FUTURE TREATMENT FOR CUSTOMER U-2-923407   65 | $1239.00 |
|---|---|

FIG. 5

| PREVENTATIVE TREATMENT IDENTIFIER 56 | PRESENT COST OF PREVENTATIVE TREATMENT 67 | OVERALL EXPECTED PRESENT VALUE OF FUTURE COST WITH PREVENTATIVE TREATMENT 68 | BENEFIT FROM PROVIDING PREVENTATIVE TREATMENT 69 | NET VALUE (BENEFIT - COST) 70 |
|---|---|---|---|---|
| PC-1-0982345 | $80.00 | $1220.00 | $19.00 | -$61.00 |
| PC-2-0982345 | $75.00 | $1238.00 | $1.00 | -$74.00 |
| PC-3-0982345 | $50.00 | $826.00 | $413.00 | +$363.00 |
| PC-5-0982345 | N/A | $811.00 | $428.00 | +$428.00 |
| PC-8-0982345 | $30.00 | $1233.00 | $6.00 | -$24.00 |

OFFER DETERMINATION DATABASE FOR CUSTOMER U-2-923407

| CUSTOMER IDENTIFIER 71 | PREVENTATIVE TREATMENT OFFERED 72 | BENEFIT OFFERED 73 | OFFER ACCEPTED? 74 | PREVENTATIVE TREATMENT ADMINISTERED? 75 |
|---|---|---|---|---|
| U-1-923407 | PC-2-0982345 | $50 OFF THE PRESENT TRANSACTION | YES | YES |
| U-2-923407 | PC-3-0982345 | ONE ROUND OF GOLF AT PEBBLE BEACH | YES | PENDING |
| U-3-923407 | PC-5-0982345 | $200.00 CASH | NO | NO |
| U-4-923407 | PC-4-0982345 | 500 FREQUENT FLYER MILES | YES | YES |
| U-5-923407 | PC-6-0982345 | GIFT CERTIFICATE FOR A DAY AT A SPA | PENDING | PENDING |

FIG. 7

SYSTEM, METHOD AND APPARATUS FOR ENCOURAGING THE UNDERTAKING OF A PREVENTATIVE TREATMENT

CROSS-REFERENCE TO RELATED APPLICATIONS

The present application claims the benefit of U.S. Provisional Patent Application Ser. No. 60/208,752 entitled "Incent Preventative Healthcare" filed on Jun. 2, 2000 in the name of Walker et al.

FIELD OF THE INVENTION

The present invention is directed generally to data processing including cost/price determination, and more particularly to an incentive or promotion program related to preventative treatment.

BACKGROUND OF THE INVENTION

With continuing advancements in the medical arts, it is possible to detect the onset of many serious conditions long before they become life-threatening. In addition, the behavior of certain individuals may be used to predict certain conditions to which they may be susceptible. However, many people are reluctant to undertake preventative treatments or early detection tests for a variety of reasons, such as fear of diagnosis, the cost of the treatment, the unpleasantness associated with certain tests, lack of time to seek treatment or an indifference to possible future health problems.

Nonetheless, it would be beneficial to insurers, primary health care providers and individuals if more people would adopt such preventative treatment on a more regular basis. By undergoing preventative treatment, a customer may avoid more serious health problems in the future. This, in turn, may decrease future costs to insurers, who would have to cover the typically expensive treatments associated with serious diseases.

Many insurers now offer to pay for the cost of preventative treatments undertaken by their insureds. Examples of preventative treatments may include blood pressure screenings, blood tests, cancer screenings, receiving a test or a diagnosis, teeth-cleaning, mammograms, pap smear tests, sigmoidoscopies, colonoscopies, immunizations, psychiatric examinations, psychological examinations, dental examinations and physical examinations. However, this is often insufficient to encourage reluctant people to adopt such preventative treatments, since the cost of the treatment is only one factor which discourages people from seeking treatment.

Insurance companies also typically offer lower premiums to people who adopt a healthy lifestyle, e.g. those who regularly visit a gym, maintain a proper diet, refrain from cigarette smoking or dangerous activities, etc. However, a discount in health insurance premiums only rewards those inclined to practice a healthy lifestyle in the first place and does little to motivate others to adopt such healthy practices.

There also exist many corporate wellness programs by which companies seek to encourage employees to adopt healthier lifestyles by providing rebates on gym memberships, lower premiums on health insurance, and the like. Again, however, such programs typically reward only those who are pre-disposed to healthy lifestyles and do not provide enough incentive to motivate others to adopt such practices.

Accordingly, there is a need for a method and apparatus for encouraging the undertaking of preventative treatments which addresses certain problems in existing technologies.

SUMMARY OF THE INVENTION

The present invention is directed to particular features of a system, method and apparatus for encouraging the undertaking of preventative treatment through the provision of transaction benefits or subsidies. In particular, one aspect of the invention includes a system, method and apparatus for providing a benefit to a customer. In one such embodiment, an insurer or other interested third party receives an identification of a customer involved in a transaction. The customer may have corresponding profile information related to, e.g., the customer's medical history. The profile information may alternatively relate to a repair or maintenance history of, for example, an appliance or item, such as a motor vehicle, owned by or in the control of the customer. The insurer then determines a preventative treatment that may be adopted by the customer. If the customer adopts the preventative treatment, the insurer may offer a benefit to the customer for the transaction, such as a subsidy toward the cost of the transaction.

According to a second aspect of the present invention, a system, method and apparatus for providing a subsidy toward a transaction allows an insurer, or other interested party to receive an identification of a transaction between a customer and a third party. The insurer transmits an identification of a preventative treatment to the customer or merchant and receives an indication that the preventative treatment has been adopted by the customer. The insurer may then provide a benefit toward the transaction.

According to a third aspect of the present invention, a system, method and apparatus for providing a benefit allows an insurer or other interested party to receive identification of a transaction between a customer and a third party, wherein profile information is associated with the customer. The insurer may then determine a preventative treatment based on the profile information. The insurer may then transmit an identification of the preventative treatment and an identification of an available benefit to the customer. Upon receiving an indication that the preventative treatment has been adopted by the customer, the insurer may provide the benefit to the customer or the third party in response to the indication.

According to a fourth aspect of the present invention, a system, method and apparatus for providing a subsidy toward a transaction allows an insurer, or other interested party, to receive an identification of a transaction request from a merchant, the transaction request including an identification of a customer who is associated with profile information. The insurer may then determine one or more preventative treatments based on the profile information and may further determine a future savings corresponding to the preventative treatment. The insurer may then transmit an identification of the preventative treatment to the customer or the merchant. The insurer may then receive an indication that the preventative treatment has been adopted by the customer, after which, the insurer may provide a currency value to the customer or merchant for the transaction request.

BRIEF DESCRIPTION OF THE DRAWINGS

Further aspects of the present invention will be more readily appreciated upon review of the detailed description of the embodiments included below when taken in conjunction with the accompanying drawings, of which:

FIG. 3 is a tabular representation of an exemplary customer database that may be stored at the controller of FIG. 2;

FIG. 4 is a tabular representation of an exemplary preventative treatment database that may be stored at the controller of FIG. 2;

FIG. 5 is a tabular representation of an exemplary expected future cost database that may be stored at the controller of FIG. 2

FIG. 6 is a tabular representation of an exemplary offer determination database that may be stored at the controller of FIG. 2

FIG. 7 is a tabular representation of an exemplary offer database that may be stored at the controller of FIG. 2

DETAILED DESCRIPTION OF THE INVENTION

Figure 1:
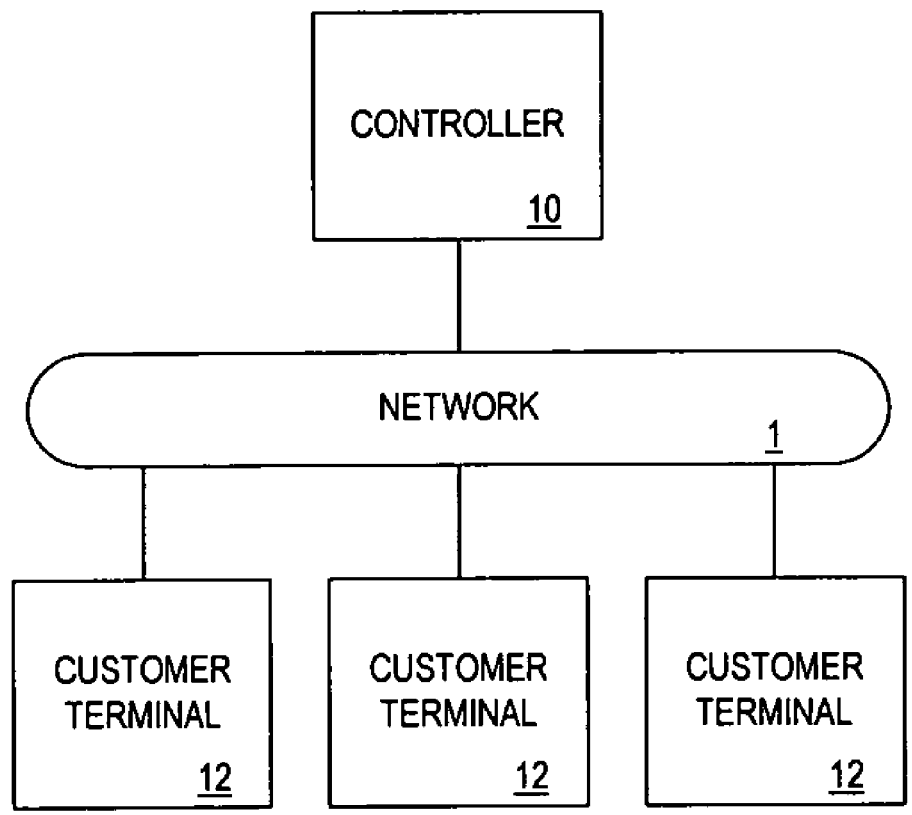
FIG. 1 is a block diagram of an exemplary system in accordance with an embodiment of the present invention.

According to various embodiments of the present invention, a customer may receive a benefit in exchange for adopting a preventative treatment. For example, a customer may visit a merchant web site on the Internet. The customer may then choose to purchase a particular item at an advertised sale price, or express interest in entering such a transaction. The merchant may then make available an option to have the customer's insurer provide a benefit applicable toward the transaction, such as a currency amount applicable toward all or a portion of the sale price. The customer may select this option, by providing an identification of the transaction (e.g. a transaction request) to the insurer. The insurer may be a present insurer of the customer or may be selected in the future by the customer. The insurer, in turn, may determine a preventative treatment applicable to the customer. The preventative treatment may be selected by the insurer according to a profile of the customer's medical history. In exchange for the customer adopting the preventative treatment, the insurer may provide the benefit to the customer or to the merchant for application towards the transaction.

As used herein, the term "preventative treatment" refers to a treatment that may help prevent or mitigate an existing or future medical condition or other injury. The treatment may include the customer (i) undertaking or agreeing to undertake a test or a physical examination which may identify a potential problem or condition, (ii) adopting a one-time or continuous maintenance program to prevent a future condition or injury, and/or (iii) adopting a one-time treatment that eliminates the need for further repeated treatments. These terms may refer to a medical or non-medical treatment, and may further include an agreement to refrain from one or more hazardous activities, such as smoking, speeding or extreme skiing. According to certain embodiments, preventative treatments offered to a customer may be based on accepted medical practices relating to one or more medical conditions. According to other embodiments, preventative repairs may be offered to a customer based on appliances or items owned by the customer, and accepted practices for maintaining such items or appliances.

As used herein, the term "expected future cost" refers to an actual, calculated, assumed or expected cost to an insurer or other interested party for treating a future condition or injury (based on measurements of typical costs incurred in treating particular conditions or injuries, and predictions of how those costs may vary in the future) multiplied by the probability that the condition or injury will occur. Other factors, such as a particular risk associated with a particular customer, the likelihood that the customer will be insured by the insurer at the time a cost for treatment is incurred, deductibles in insurance coverage, conditions which are not insured, the probability that the preventative treatment will alleviate the onset of a future condition or detect further conditions, and the length of time before such conditions may be contracted may all be factored into the calculation of the future cost.

"Expected present value of future cost," as used herein, refers to the expected future cost discounted to a present value in any manner well known to those of skill in the art.

As referred to herein, a customer may adopt a preventative treatment by undertaking the preventative treatment, agreeing to undertake the preventative treatment, or agreeing to undertake the preventative treatment within a predetermined time.

As used herein, the term "customer" refers to an individual or a group of individuals making a purchase, an individual or group of individuals operating a customer terminal, or a party insured by an insurer. The party insured by an insurer may be an insurance policy holder, or a party covered by another's insurance policy, such as a dependent of an insured party. "Customer" may also refer to more than one party receiving a benefit.

As used herein, the term "benefit" may refer to a subsidy toward a transaction or a purchase total, an item having a predetermined value, or a currency value. The benefit may further be "penalty-secured" which may involve, for example, an authorization to charge a customer's credit card account if the preventative treatment is not undertaken.

It should be recognized that one preventative treatment may be prescribed for one or more conditions and that many preventative treatments may be applied for one condition.

Referring now to FIGS. 1-10, wherein similar components of the present invention are referenced in like manner, embodiments of a system, method and apparatus for encouraging the undertaking of preventative treatment through the provision of transaction benefits or subsidies are disclosed.

Turning now to FIG. 1, there is depicted a plurality of customer terminals 12 which may be used to communicate with one or more controllers 10 via a computer network 1. Computer network 1 may be an Internet-based network such as the World Wide Web, or it may be any one or more of a local area network (LAN), a wide-area network (WAN), an intranet environment, an extranet environment, a wireless network or any other type of computer network, such as those enabled over public switched telephone networks.

In certain embodiments, a customer terminal 12 may be operated by a customer and the controller 10 may be operated by an insurer or other party who may realize a savings in future expenditures by encouraging the customer to adopt a preventative treatment. Accordingly, controller 10 may be embodied as a computer server, or a system of computer servers, operated by an insurer or another party who performs various methods of the present invention as disclosed herein. Customer terminals 12 may each be any type of computing device, such as a personal computer, a workstation, a network terminal, a hand-held remote access device, a point-of-sale terminal, a kiosk, a personal digital assistant (PDA) or any other device or combination of devices that can accomplish two-way electronic communication over the network connection.

Controller 10 and/or customer terminals 12 may each additionally communicate with other remote computers, such as a merchant terminal (not shown), a third party payment processing server (not shown), a referrer terminal (not shown), or other devices in order to achieve various purposes of the present invention. Further functions and operations of controller 10 and customer terminals 12 are discussed in detail below.

Figure 2:
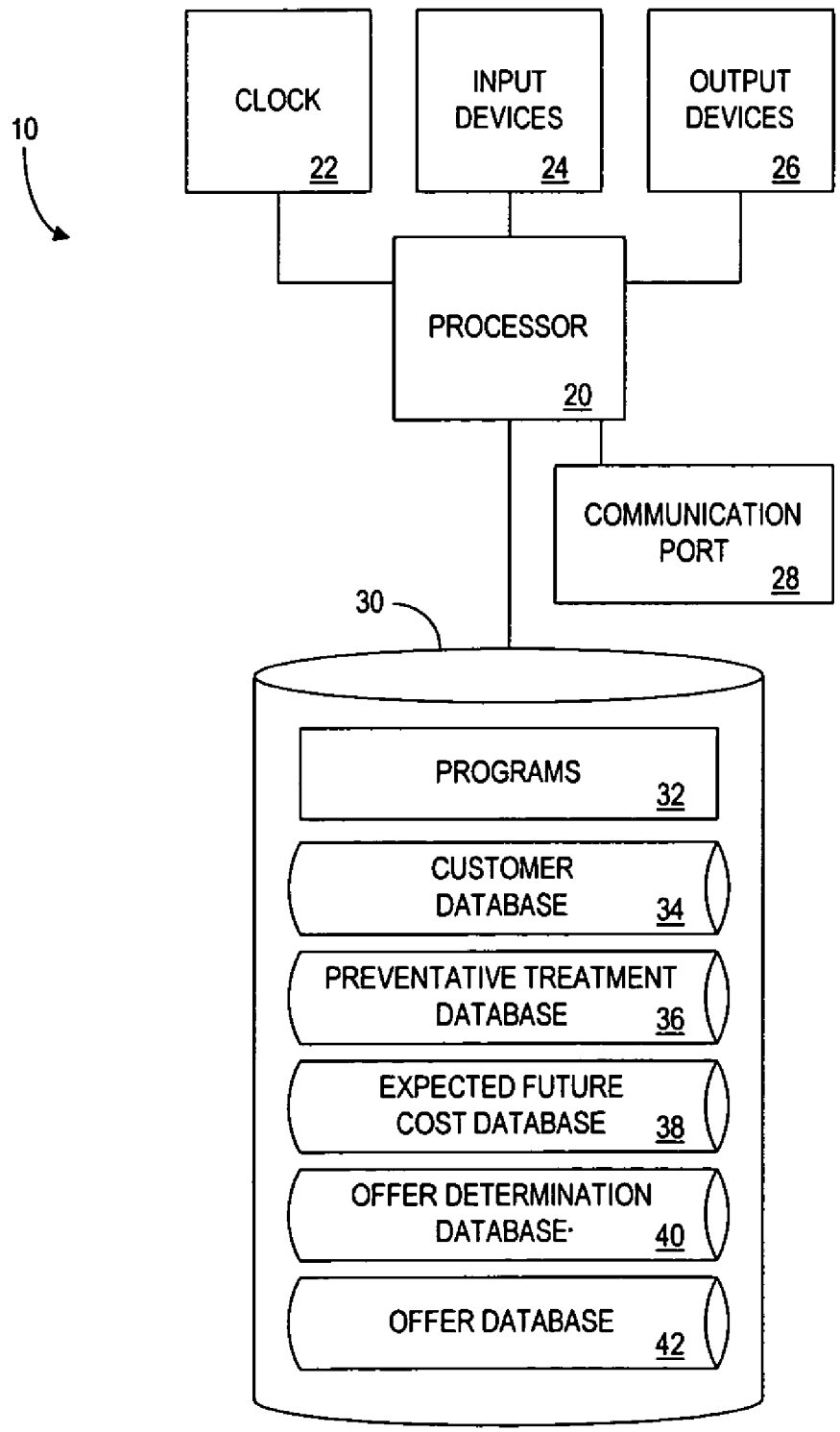
FIG. 2 is a block diagram of an exemplary controller used in the system of FIG. 1.

Turning now to FIG. 2, exemplary components of a computing device, such as a controller 10, are shown. It should be understood that any of the customer terminals 12 may share similar features with the controller 10. However, for the sake of brevity, the discussion immediately below will refer to the controller 10 only. The controller 10 may be implemented as a system controller, a dedicated hardware circuit, an appropriately programmed general purpose computer, or any other equivalent electronic, mechanical or electro-mechanical device.

The primary component of the controller 10 is a processor 20, which may be one or more of any commonly available microprocessor, such as the PENTIUM III manufactured by INTEL CORP. If the processor 20 comprises a plurality of microprocessors, the plurality of microprocessors may or may not operate in parallel. The processor 20 may be operatively in communication with further exemplary components, such as a clock 22, input devices 24, output devices 26, a communication port 28 and a memory 30. The memory 30, in turn, may store one or more computer programs 32, a customer database 34, a preventative treatment database 36, an expected future cost database 38, an offer determination database 40 and an offer database 42.

The processor 20 and the memory 30 may each be (i) located entirely within a single computer or other computing device; (ii) connected to each other by a remote communication medium, such as a serial port cable, telephone line or radio frequency transceiver; or (iii) a combination thereof. In one embodiment, the controller 10 may comprise one or more computers that are connected to a remote server computer for maintaining databases.

The processor 20 may operate in conjunction with random access memory (RAM) and read-only memory (ROM) in a manner well known in the art. The random-access memory (not shown) portion of the RAM/ROM memory may be a suitable number of Single In-line Memory Module (SIMM) chips having a storage capacity (typically measured in kilobytes or megabytes) sufficient to store and transfer, inter alia, processing instructions utilized by the processor 20 which may be received from the computer programs 32. The read-only memory (not shown) portion of the RAM/ROM memory may be any permanent, non-rewritable memory medium capable of storing and transferring, inter alia, processing instructions performed by the processor 20 (e.g., during a start-up routine of the controller 10).

The clock 22 may be an on-board component of the processor 20 which dictates a clock speed (typically measured in MHz) at which the processor 20 performs and synchronizes, inter alia, communication between the internal components of the controller 10.

The input devices 24 may be one or more commonly known devices used for receiving operator inputs and the like. Accordingly, exemplary input devices 24 may include a keyboard, a mouse, and/or a voice recognition unit. Output devices 26 may include any commonly known devices used to present data to an operator of the controller 10 or to transmit data over the computer network 1 to customer terminals 12. Accordingly, suitable output devices may include a display, a printer and/or a voice synthesizer connected to a speaker.

Communication port 28 may include a telephonic or network connection device, such as a telephone modem, a cable modem, a T-1, T-2 or T-3 connection, a digital subscriber line or a network card, for communicating data to and from other computer devices over the computer network 1. According to an embodiment involving a network server, it is contemplated that the communications devices used as communication port 28 may have the capacity to handle high bandwidth traffic in order to accommodate communications with a large number of customer terminals 12, as well as other remote devices.

The memory 30 may be an internal or external large capacity device for storing computer processing instructions, computer-readable data, and the like. The storage capacity of the memory 30 may typically be measured in megabytes or gigabytes. Accordingly, the memory 30 may be one or more of the following: a floppy disk in conjunction with a floppy disk drive, a hard disk drive, a compact disc-read only memory (CD-ROM) medium and reader/writer, a digital video disk (DVD) and reader/writer, a ZIP disk and a ZIP drive of the type manufactured by IOMEGA CORP., and/or any other computer readable medium that may be encoded with processing instructions in a read-only or read-write format. Further functions of and available devices for memory 30 will be apparent.

The memory 30 stores, inter alia, a plurality of programs 32 which may be any one or more of an operating system such as WINDOWS 2000 by MICROSOFT CORP, and one or more application programs, such as a Web hosting program, and a database management program of the type manufactured by ORACLE, each of which may be necessary to implement the embodiments of the present invention. The programs 32 include processing instructions for accomplishing communication between customer terminals 12 and the controller 10, as described herein. Accordingly, the programs 32 may further include a Web hosting application, and the like, for allowing customers to submit information, such as transaction requests (e.g. information regarding a transaction between the customer and a merchant), to the controller 10, to receive information regarding benefits or subsidies that are available through the controller 10 for the transaction, and the like. The Web hosting software may include functionality sufficient to read JAVASCRIPT, HTML, XML and/or other similar programming languages typically used in conjunction with Internet applications.

The programs 32 furthermore include program elements that may be necessary, such as an operating system, a database management system and "device drivers" for allowing the processor 20 to interface with computer peripheral devices. Appropriate device drivers and other necessary program elements are known to those skilled in the art, and need not be described in detail herein. The programs 32 may also include other applications, such as VISUAL BASIC, to allow an operator to program specific functions to be performed by the controller 10, as described herein.

The memory 30 may also store a plurality of relational databases, such as a customer database 34, a preventative treatment database 36, an expected future cost database 38, an offer determination database 40 and an offer database 42, examples of which are depicted in FIGS. 3-7, as described below. In referring to the databases depicted therein, it is important to note that the first row of each database includes a field header for each field of the database and the remaining rows each correspond to one record of the database. Fields of data are represented by each column. Further or fewer fields and records of data may be used. The databases presented herein may also be re-configured into any number of relational databases. In addition, configurations other than standard database formats may be used to store the data maintained in exemplary databases 34-42.

The term "computer-readable medium" as used herein refers to any medium that directly or indirectly participates in providing instructions to processor 20 for execution. Such a medium may take many forms, including but not limited to, non-volatile media, volatile media, and transmission media. Non-volatile media include, for example, optical or magnetic disks. Volatile media include dynamic random access memory (DRAM), which typically constitutes the main memory. Transmission media include coaxial cables, copper wire and fiber optics, including the wires that comprise a system bus coupled to the processor 20. Transmission media can also take the form of acoustic, electrical or electromagnetic waves, such as those generated during radio frequency (RF) and infrared (IR) data communications.

Some common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave such as electrical, electromagnetic or optical signals, or any other medium from which a computer can receive processing instructions.

Various forms of computer readable media may be involved in carrying one or more sequences of one or more instructions to the processor 20 for execution. The following example illustrates the transmission of computer-readable instructions via a plurality of media. The instructions may initially be stored on a magnetic disk of a remote computer. The remote computer can load the instructions into its dynamic memory and send the instructions over a telephone line using a modem. A modem local to the controller 10 can receive the instructions from the telephone line and use an infrared transmitter to convert the instructions into an infrared signal. An infrared detector can receive the instructions represented by the infrared signal and transmit the instructions across a system bus to processor 20. The system bus carries the instructions to main memory, from which processor 20 retrieves and executes the instructions. The instructions received by main memory may optionally be stored elsewhere before or after execution by processor 20.

Referring now to FIG. 3, an exemplary customer database 34 is provided to store profile information and identification data pertaining to a customer. In particular embodiments, the customer may be a party who is insured by an insurer, and the profile information may include, e.g., a medical history of the customer, including health-related statistics of the customer. Accordingly, customer database 34 is shown to include a customer identification field 50, a customer name field 51, an age field 52, a smoker field 53, a drinker field 54 and a field for indicating family medical history problems 55.

The customer identification field 50 may contain data representing a unique identifier pertaining to a particular customer. The identifier may be any alphabetic, numeric or alphanumeric code sufficient to uniquely identify a customer. The code may be generated by the controller 10, assigned by the operator of the controller 10, or selected by the customer. In particular embodiments wherein the operator is an insurer or potential insurer of the customer, the code may correspond to an insurance policy number assigned to an insurance policy held by the customer and serviced by the insurer.

The customer name field 51 may contain data representing the actual name of a customer. The customer name field 51 may contain further identification or contact data pertaining to the customer, such as an address or telephone number corresponding to the customer.

The age field 52 may contain data representing an age of the customer, which may be used by the operator of the controller 10 to determine a suitable preventative treatment as discussed further hereinbelow.

Fields 53-55 may contain data representing further profile information corresponding to each customer, which, in turn, may be used to determine a suitable preventative treatment to be undertaken by the customer. The information may be obtained from the customer, or through any source having such information, and is preferably obtained with the customer's consent. Smoker field 53 may contain data representing an indication of whether the customer uses tobacco or tobacco-related products. Drinker field 54 may contain data representing an indication of whether the customer consumes alcoholic beverages. History of disease field 55 may contain data representing an indication of whether the customer's family has a history of one or more predetermined medical conditions, such as heart disease. As will be appreciated by one of ordinary skill in the art, other fields may be included within customer database 34, such as a field for indicating whether the customer undertakes other hazardous activities (such as extreme skiing, speeding, skydiving and the like), whether the customer currently receives other preventative treatments, and/or whether the need for preventative treatments to be administered in the future have previously been identified.

Turning now to FIG. 4, therein is depicted an exemplary preventative treatment database 36 as may be stored by the controller 10 of FIG. 2. The preventative treatment database 36 is provided to store information relating to a list of preventative treatments that may be offered to or selected by a customer in exchange for receiving a benefit, such as a subsidy during a transaction. Accordingly, the preventative treatment database 36 may include a preventative treatment identifier field 56, a description of preventative treatment field 57, a preventative treatment cost field 58, a first result of preventative treatment field 59 and a second result of preventative treatment field 60.

Preventative treatment identifier field 56 may contain data representing a unique identifier pertaining to a preventative treatment to be offered to a customer. The identifier may be any alphabetic, numeric or alphanumeric code sufficient to uniquely identify a treatment. The code may be generated by the controller 10 or assigned by the operator of the controller 10.

Description of preventative treatment field 57 may contain data representing a written description of each preventative treatment that may be offered by the controller 10. Such descriptions may be transmitted or indicated to a customer over computer network 1 in order to determine whether the customer is interested in receiving a subsidy toward a transaction or other benefit for adopting the preventative treatment.

Cost field 58 may contain data representing an indication of the cost of each preventative treatment stored by the controller 10. The cost may be determined in any manner known in the art, or may represent an average expected present cost of a treatment if undertaken by a customer.

Fields 59 and 60 store data representing descriptions of primary and secondary benefits, respectively, that may result from customers undertaking the preventative treatment. These results may be used to determine an expected future savings associated with the preventative treatment, as described further hereinbelow. Additional fields containing further benefits of each treatment may be provided as well.

FIG. 5 depicts an exemplary expected future cost database 38 having a plurality of records which may be stored at the controller of FIG. 2. In an embodiment involving health treatments, the expected future cost database 38 may be provided to store, for each customer, information related to a set of possible conditions that the customer may contract, based on the customer's age, personal habits or family history, as well as general health statistics of the population at large. Accordingly, expected future cost database 38 may contain a cost of future treatment field 61, a present value of cost of future treatment field 62, a probability that future treatment will be necessary field 63, an expected present value of the cost of future treatment field 64, and an overall expected present value of cost of future treatment field 65.

Cost of future treatment field 61 may contain data representing a description of a treatment for a condition or injury that a customer may contract or suffer in the future. The conditions or injuries for which treatments are listed for each customer may be determined from the customer's profile information, general population statistics or a combination of the same. In an embodiment where the operator of controller 10 is a health insurance provider and the customer is an insured or potential insured of the provider, the data representing treatments stored in field 61 may be for medical conditions to which the customer may be susceptible. According to further embodiments, the operator of the controller 10 may be an automobile insurance provider, in which case the data stored in field 61 may include representation of, for example, treatment for injuries to the customer resulting from an automobile accident, treatments for injuries to others from an automobile accident caused by the customer, repairs for damage to a customer's automobile resulting from an automobile accident, routine maintenance to offset mechanical failure, and the like. Further examples will be apparent to one of ordinary skill in the art.

Present value of cost of future treatment field 62 may contain data representing an indication of a present value of a future cost pertaining to each listed treatment. These values may be determined from statistics relating to the cost of a treatment for the condition, including future projections of historical costs of treating the condition. These values may be determined in part based on the anticipation of future improvements in medical technology that will become available for treating the conditions and of the cost of this technology.

Field 63 stores data representing a probability that the corresponding future treatment in field 61 will become necessary for the customer. The probability may be determined from the customer's profile information, general population statistics and the like.

Expected present value of cost of future treatment field 64 stores, for each listed future treatment, data representing the value of field 62 multiplied by the probability stored in field 63. The sum of all the values stored in field 64 may be saved in the overall expected present cost of future treatment field 65 for each customer listed in customer database 34. The value in field 65 may be used to determine a benefit or subsidy amount available to a customer involved in a transaction, or may be used to eliminate inefficient preventative treatments, and may be further conditioned upon the customer agreeing to undertake preventative treatment regarding the prescribed conditions determined for that customer. The entire value in field 65, or any portion thereof, may be provided to the customer at the discretion of the insurer, as described further below.

Turning to FIG. 6, an exemplary offer determination database 40, and exemplary records thereof, may be provided to store preventative treatments and associated costs determined for a particular customer from the data in expected future cost database 38. Accordingly, the offer determination database 40 may contain a preventative treatment identifier field 56, a present cost of preventative treatment field 67, an overall expected present value of future cost with preventative treatment field 68, a benefit from providing preventative treatment field 69 and a net value of the preventative treatment field 70.

Preventative treatment identifier field 56 may store data representing an identifier of a preventative treatment determined to be applicable to a particular customer. The identifier may correspond to those described above with respect to FIG. 4.

Present cost of preventative treatment field 67 may contain data representing the present cost for the treatment, and may further correspond to the values described above with respect to cost field 58 of preventative treatment database 36, as shown in FIG. 4.

Overall expected present value of future cost with preventative treatment field 68 stores data representing the value stored in overall expected cost of future treatment field 65 adjusted for the customer receiving the preventative treatment identified in field 56. For example, if the customer identified as U-2-923407 were to undertake a dental cleaning (corresponding to preventative treatment identifier PC-1-0982345), as a first result of preventative care 59, this will reduce the customer's risk of developing cavities by 40%. This will, in turn, reduce the probability that the customer will require the future treatment 61 of having a dental cavity filled. The probability that this future treatment will be necessary 63 will be reduced from 15% to 9%. This adjusted probability multiplied by the present value of the cost of filling a dental cavity in the future 62 of $320.00, yields a new expected present value of the cost of filling a dental cavity in the future 64 of $28.80. This then changes the overall cost of present value of future treatment for customer U-2-923407 from the original value of $1239.00 to an adjusted value of $1219.80. This adjusted value is stored in offer determination database 40 for the customer U-2-923407 in the overall expected present value of future cost with preventative treatment field 68 that corresponds to the preventative treatment identifier 56 PC-1-0982345. (In the figure, the value $1219.80 has been rounded up to $1220.00) The value stored in field 68 may then be used to determine a net benefit of offering a subsidy to the customer in exchange for adopting the preventative treatment, as described further below.

The benefit from providing the preventative treatment field 69 stores data representing a value corresponding to the amount by which administering the preventative treatment decreases the overall expected present value of the future cost associated with a customer, i.e., the value stored in field 69 equals the value stored in field 65 minus the value stored in field 68.

The net value of preventative treatment field 70 stores data representing the difference between the values stored in field 69 and field 67. This value from field 70 may be used by the operator of the controller 10 to determine which preventative treatments are most efficient to offer to the customer. The value stored in field 70 may be used to determine the value of a benefit offered to a customer, should the customer adopt the corresponding preventative treatment. For example, the operator of the controller 10 may determine that only those preventative treatments with a positive value stored in field 70 are to be offered to a customer.

Turning now to FIG. 7, therein is depicted an exemplary offer database 42 which may be provided to store data representing a list of preventative treatments previously offered to various customers. Thus, if desired, the offer database 42 may be used to guard against a customer repetitively and undesirably undertaking the same preventative treatment in order to surreptitiously receive the benefit more than once. The offer database 42 may be further used to confirm that a preventative treatment accepted by a customer has actually been undertaken. Accordingly, offer database 42 contains a customer identifier field 71, a preventative treatment offered field 72, a benefit offered field 73, an offer accepted field 74 and a preventative treatment administered field 75.

Customer identifier field 71 stores data representing the unique identifier of each customer who was offered a benefit or subsidy toward a transaction in exchange for undertaking a preventative treatment. The values represented in field 71 of FIG. 7 correspond to certain of the identifiers stored in customer identifier field 50 of database 34 of FIG. 3.

The preventative treatment offered field 72 may contain data representing an identifier of a preventative treatment offered to the respective customer. The identifier in this field 72 may correspond to certain of the identifiers stored in field 56 of database 36, as described above.

The benefit offered field 73 may contain data representing a description of the benefit offered to the customer in exchange for undertaking the respective preventative treatment. The benefit offered may correspond to the net value stored in net value field 70 of offer determination database 40, or any portion of the value stored therein.

The offer accepted field 74 may contain data representing an indication of whether the offer was accepted by the customer. The values in this field may be used to prevent the operator of controller 10 from providing the same offer to the same customer on the basis of the customer's acceptance or rejection of the offer.

Preventative treatment administered field 75 may contain data representing an indication of whether the customer actually undertook the respective preventative treatment. According to one embodiment, a confirmation of the administration of the treatment may be provided to the operator of the controller 10 by a health care provider, such as a doctor, a hospital or a medical clinic. The health care provider may be compensated by the operator or insurer for the administrative work of providing the confirmation. The confirmation may likewise be derived from a claim submitted by the customer to the insurer for the cost of the preventative treatment.

Other manners of confirming the administration of the preventative treatment may likewise be used. For example, according to one embodiment, the party providing the preventative treatment may, upon the customer's completion of the treatment, give the customer a code confirming that the customer received the treatment. The customer may then give this code to the operator of the controller as a confirmation that the preventative treatment was administered to the customer. In order to circumvent fraudulent use, the code may be unique for each transaction involved and/or may be confirmed or authenticated by the operator upon receipt.

Figure 8:
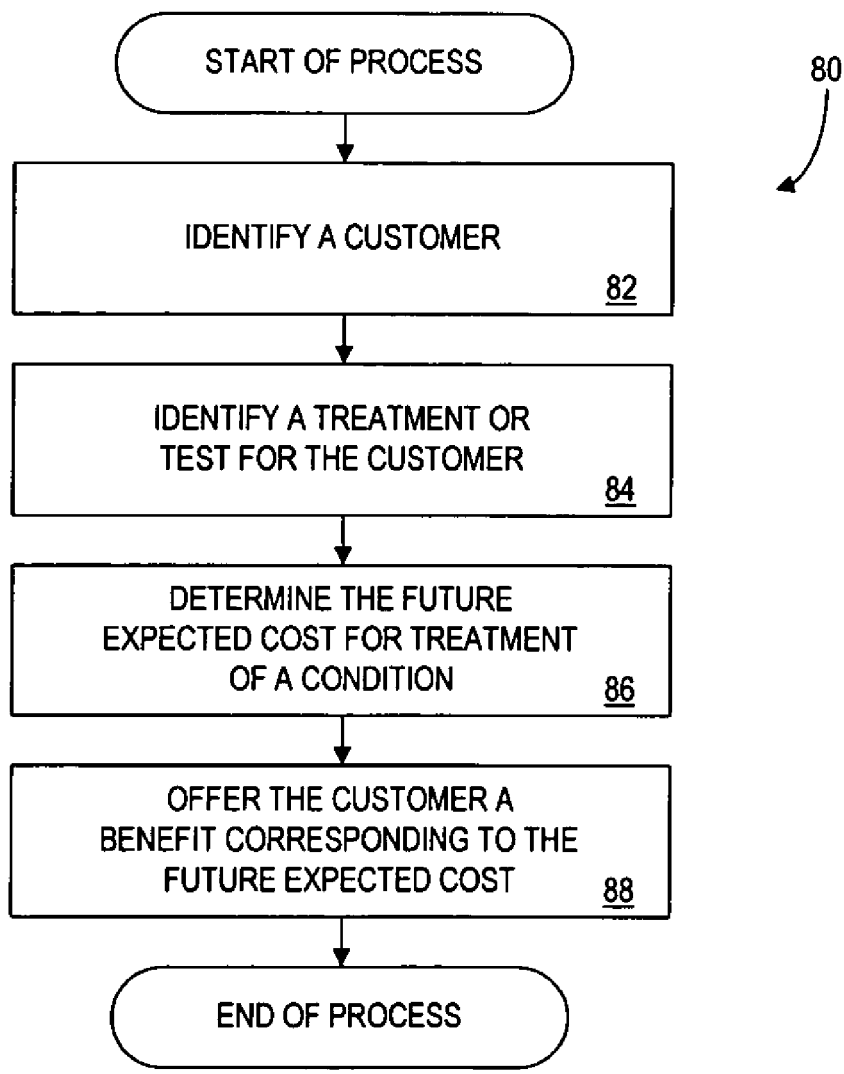
FIG. 8 is a flow chart depicting a method for determining a benefit according to an embodiment of the present invention.

Referring now to FIG. 8, therein is depicted a first exemplary process 80 for offering a benefit to a customer involved in a transaction in exchange for the customer adopting a preventative treatment. The process 80 begins at step 82 where a customer is identified to the controller 10, e.g., via the computer network 1. The customer may be identified by the customer himself, a merchant involved in a transaction with the customer, or a referrer who refers the customer to the operator of the controller 10, such as a friend or a family member of the customer. In alternate embodiments, the customer may receive a benefit for referring a third party rather than undertaking the preventative treatment him or herself.

Additionally, in an embodiment where the customer is involved in a transaction with a merchant, transaction information may also be identified, including a product or service being purchased by the customer and the cost of the product or service.

Next, the controller 10 uses the customer's profile data, as stored in customer database 34, to determine a preventative treatment or test that may be applicable to the identified customer (step 84). As stated previously, the preventative treatment may be determined from the customer's profile information, general population statistics, or a combination thereof.

The controller 10 may then determine the expected future cost for the identified customer if he or she does not undertake one or more prescribed preventative treatments (step 86). The expected future cost corresponds to the actual, average or expected costs of treating a given condition in the future.

Figure 9:
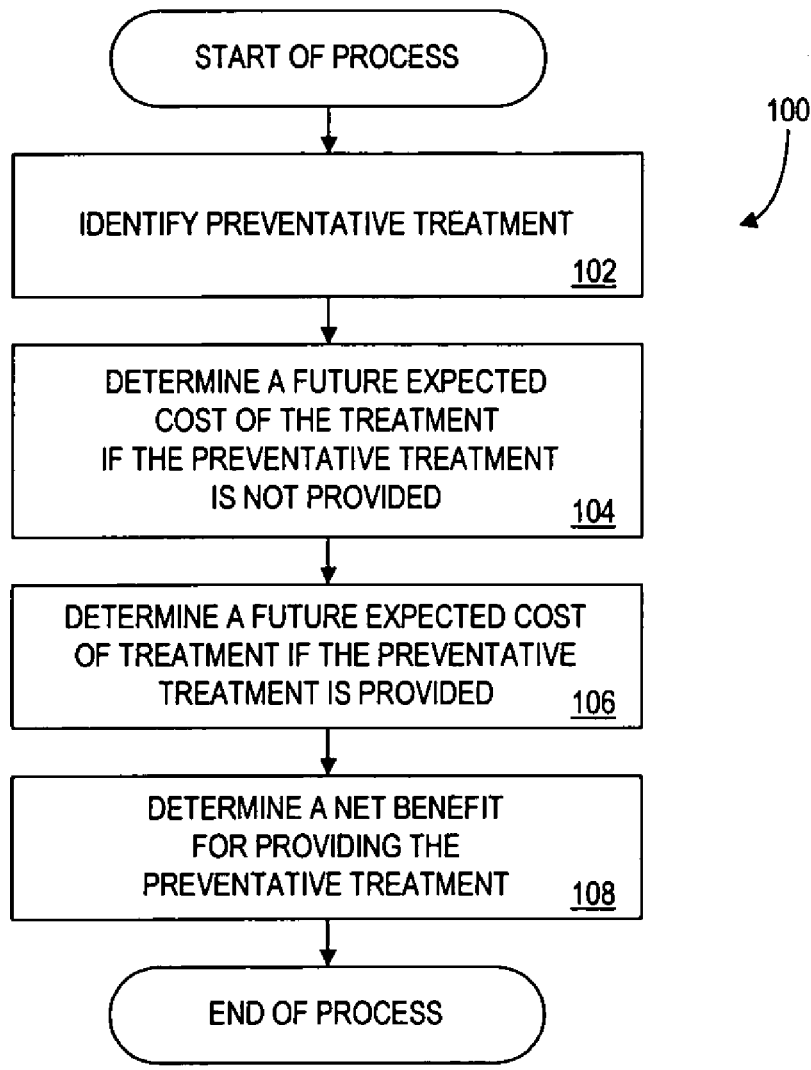
FIG. 9 is a flow chart depicting a method for determining a net benefit to an insurer for a customer receiving a preventative treatment according to an embodiment of the present invention.

The controller 10 may then transmit an offer to the identified customer (step 88). An example of such an offer may be, for example, a customer with a family history of heart disease may be offered $50 toward a purchase of an item, such as a television, in exchange for the customer undergoing a blood pressure screening. The value of the offer made may be based on the expected future cost of treating a condition, a present value thereof, or any portion of these values. The offer may be conditioned upon an agreement by the customer to undertake the identified preventative treatment. In alternate embodiments, the customer may request an alternate preventative treatment. Also, the operator of controller 10 may require that the customer "penalty-secure" the agreement, e.g., by providing a security deposit in the amount of the value of the offered benefit which may be returned to the customer upon receiving a confirmation of the administration of the preventative treatment to the customer. The security deposit may include a penalty amount that is to be retained if the preventative treatment is not undertaken. Turning now to FIG. 9, therein is depicted an exemplary process 100 for determining a net benefit of a preventative treatment. The process 100 allows an insurer to determine which of a set of preventative treatments are most efficient on the basis of costs incurred and costs avoided. The insurer may then use this determination to formulate which of a plurality of preventative treatments are to be offered to a customer according to the present invention.

The process 100 begins with the selection of a preventative treatment from a plurality of available preventative treatments contemplated for a customer (step 102). The controller 10 then determines an expected present value of a future cost of treatment if the preventative treatment is not provided (step 104). This may include determining a cost of treating a condition. The future cost may also be determined by factoring any number of probabilities including: a probability that a customer will contract the condition, a probability that the customer will still be insured by the insurer at the time the condition needs treatment, a probability that the customer will obtain the preventative treatment on his own, a probability that the insurer will still be in business at the time the customer contracts the condition, as well as general population statistics and other standard actuarial figures.

The controller 10 may then determine the expected present value of a future cost of treatment if the preventative treatment is provided (step 106). This value may be determined based on the cost of treating the condition, the cost of administering the preventative treatment, as well as the amount by which the future cost will be decreased due to the preventative treatment.

The controller 10 then may determine a net benefit for providing the preventative treatment by subtracting the value determined in step 106 from the value determined in step 104 (step 108).

The net benefit determined according to process 100 may be used to select a preventative treatment to be offered to a customer and/or to determine a value of a benefit to be offered to the customer. The net benefit for each preventative treatment may be stored in net value of preventative treatment field 70 of database 40.

Figure 10:
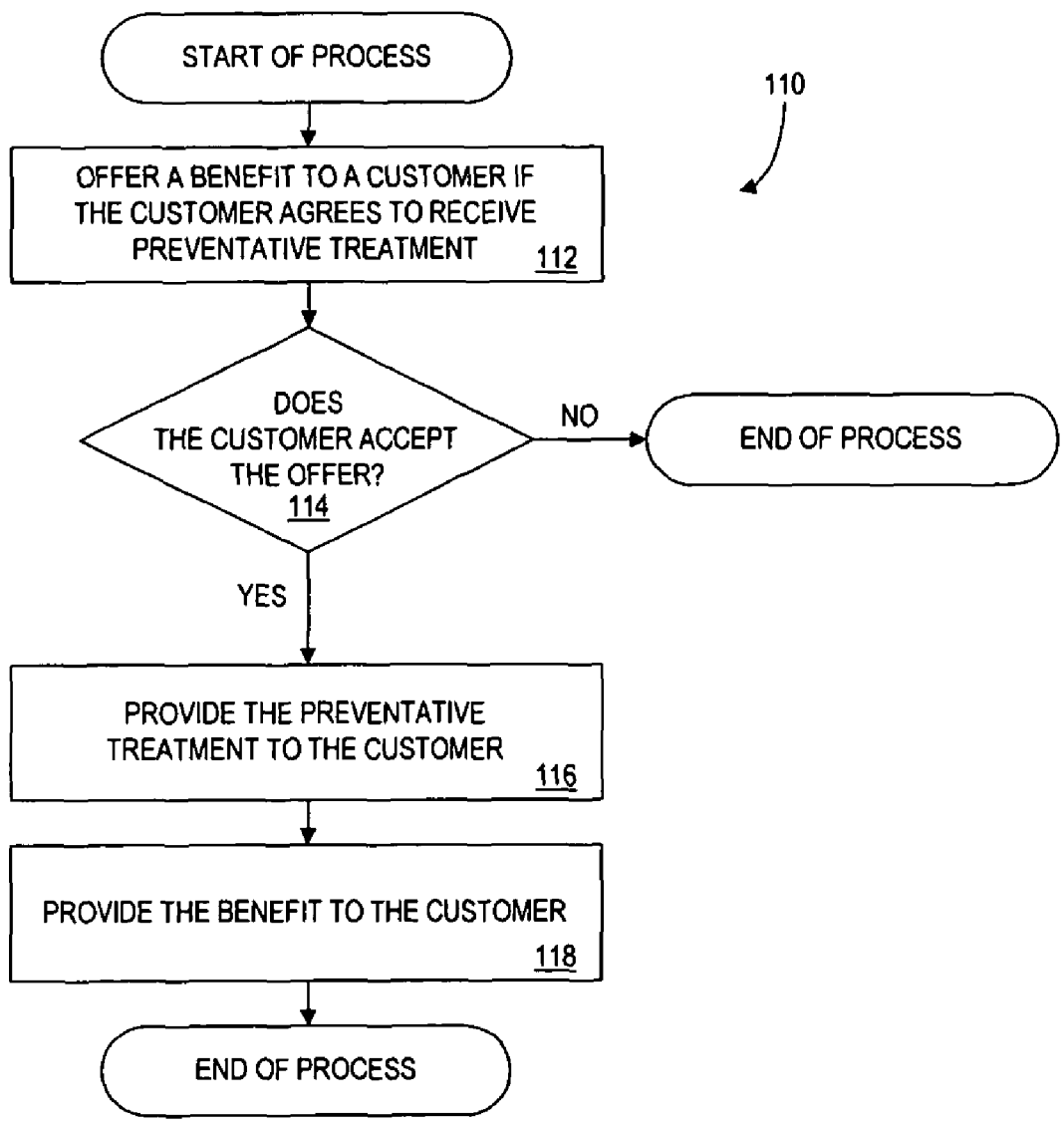
FIG. 10 is a flow chart depicting a method for providing a benefit according to an embodiment of the present invention.

Turning now to FIG. 10, therein is depicted an exemplary process 110 for providing a benefit to a customer in accordance with an embodiment of the present invention. The process 110 begins at step 112 wherein the controller 10 offers a benefit to a customer conditioned upon the customer agreeing to undertake a preventative treatment. Next, the controller determines whether the customer accepts the offer (step 114). This may be accomplished, for example, by the customer transmitting an indication of an acceptance of the offer in any known manner. If the offer is not accepted, the process 110 ends. Otherwise, process 110 continues to step 116 wherein the preventative treatment is provided to the customer. This administration of the preventative treatment may be handled by a party other than the operator of controller 10. Such parties may include a physician, a government agency (such as the National Institute for Health, a public hospital or clinic and the like), a drug manufacturer who administers a drug treatment, a medical equipment manufacturer that provides medical testing, a veterinary hospital or the like. According to an embodiment involving other types of preventative treatments, such parties may include an automobile repairman or repair center and a residential or commercial maintenance provider, or any other party in a position to administer a particular preventative treatment. These parties may, in turn, provide a confirmation to the operator of the controller 10 that the preventative treatment has been performed.

Finally, at step 118, the controller 10 provides a benefit to the customer, after which the process 100 ends. The benefit provided to the customer may be based on a net benefit of the preventative treatment, which, in turn, may be determined based on future costs avoided. The benefit may be provided in the form of cash or a currency value. However, it is contemplated that alternate forms of currency may be provided instead. Such alternate currency may include, for example, frequent flier miles and pre-paid telephone time. The benefit may be provided directly to the customer, or may be provided to a merchant with whom the customer is involved in a transaction. The benefit may further be paid at once, or in a series of installments.

According to further embodiments of the present invention, it is contemplated that the customer may receive a benefit prior to undertaking the preventative treatment. For example, the customer may agree to undertake the preventative treatment and provide a form of security corresponding to the benefit received, which may be held by the operator of the controller 10 until confirmation of the administration of the preventative treatment. Such security may be a financial account identifier, such as a credit card number, identifying an account from which a currency value may be withdrawn. The currency amount may correspond to the value of the benefit received if either the preventative treatment is not undertaken or if it is not undertaken within a predetermined period of time. The customer may also be prevented from participating in the system of the invention in the future if the treatment is not adopted.

According to further embodiments of the present invention, it is contemplated that the customer identified to the controller 10 must, in addition, agree to stay insured with the insurer for a predetermined time. This requirement prevents a customer from receiving a benefit and then switching to a new insurer who will realize the savings in the future without paying for the benefit which prompted the customer to undertake the preventative treatment.

It is further contemplated that a benefit received is contingent upon the customer being diagnosed with a certain medical condition. For example, if the customer is known to have high blood pressure, the customer may receive a benefit for taking medication to counteract the condition.

According to certain embodiments, it is contemplated that the customer being provided the offer may not be insured by the operator of the controller 10 at the time the offer is made. In such an embodiment, it is contemplated that the offer will include a condition that the customer switch insurance carriers to the insurer making the offer. The customer may also be required to receive the preventative treatment from a particular treatment provider.

According to additional embodiments of the present invention, it is contemplated that the step of identifying the customer to the controller 10 includes the provision of current medical statistics, such as the customer's profile information. Such statistics may be provided by a health care provider who treats the customer. Alternatively, the statistics may be provided by a device, such as a blood pressure monitor or a heart monitor, which may be in communication with, for example, the customer terminal 12.

According to certain embodiments, the controller 10 may be operated by an insurer. However, it is contemplated that a party other than an insurer may be interested in encouraging people to seek preventative treatment, and thus, may choose to operate such a system. In embodiments where the system is operated by a party other than an insurer, the future cost and expected future cost, rather than being a cost to an insurer for future treatment may be an analogous cost corresponding to that party. For example, if the party is a drug manufacturer, the future cost and expected future cost may be based on a cost associated with the purchase of pharmaceutical drugs to treat or prevent a condition to which the customer may be susceptible.

Examples of other such interested parties include physicians, employers, a government agency such as the Center for Disease Control or the National Institute for Health, drug manufacturers, medical equipment manufacturers, automobile repairmen or repair centers, and repairers of residential or commercial properties. The controller 10 may further be operated by more than one party, such as a group of insurers or a party representing a group of insurers. It is further contemplated that certain embodiments of the present invention will include a benefit offered to a customer based on known preferences of the customer. For example, if the customer is interested in a particular sports team, the benefit may correspond to a discount on merchandise related to that team. Other variations of customer preferences are likewise contemplated.

Certain embodiments of the present invention have been described above as involving online interaction between a customer and a controller. However, it should be readily understood that communication of information between these or any other parties may take place in other manners, such as by telephone interaction, face-to-face interactions, via mail or other courier, or in any other known manner.

It should be further apparent that any of the methods or processes described herein may be performed in the order in which they were described. However such processes or methods may be performed in any other order which accomplishes the results of the present invention.

Although the invention has been described in detail in the foregoing embodiments, it is to be understood that the descriptions have been provided for purposes of illustration only and that other variations both in form and detail can be made thereupon by those skilled in the art without departing from the spirit and scope of the invention, which is defined solely by the appended claims.

What is claimed is:

1. A method for providing a benefit to a customer, comprising:
 receiving, by a controller comprising at least one processor, an identification of a customer involved in a transaction with a third party,
  wherein the identification comprises at least one of: an identifier associated with the customer and a name of the customer;
 determining, by the controller, a preventative treatment for the customer;
 offering a benefit to the customer toward the transaction if the customer adopts the preventative treatment;
 receiving, by the controller, an indication that the customer agrees to adopt the preventative treatment; and
 providing the benefit.

2. The method of claim 1, wherein the receiving further comprises receiving the identification from at least one of: the customer, a merchant, a web site operator, an acquaintance of the customer, a family member related to the customer, a doctor, a pharmacist, an insurance provider, and a government agency.

3. The method of claim 1, wherein said customer is involved in a transaction comprising at least one of: a purchase of a product, a purchase of a service, an insurance premium, and an online purchase.

4. The method of claim 1, wherein the customer has profile information comprising at least one of:
 an age of the customer, a gender of the customer, a geographic location corresponding to a residence of the customer, a medical history of the customer, a medical history of the customer's family, an occupation of the customer, a previous preventative treatment adopted by the customer, and at least one preventative treatment not adopted by the customer.

5. The method of claim 1, wherein the preventative treatment further comprises at least one of:
 a preventative health treatment, a preventative automobile repair, and a preventative home maintenance repair.

6. The method of claim 5, wherein the preventative health treatment comprises at least one of:
 a blood test, a cancer screening, a blood pressure screening, a teeth-cleaning treatment, a mammogram, a pap smear, a sigmoidoscopy, a colonoscopy, an immunization, a psychiatric examination, a psychological examination, a dental examination and a physical examination.

7. The method of claim 1, wherein said determining a preventative treatment further comprises:
 determining the preventative treatment based on a list of preventative treatments not undertaken by the customer.

8. The method of claim 1, wherein said determining a preventative treatment further comprises:
 determining the preventative treatment based on a list of preventative treatments not undertaken by the customer within a predetermined time.

9. The method of claim 1, wherein said determining a preventative treatment further comprises:
 determining a plurality of preventative treatments, wherein the customer may adopt at least one of said plurality of preventative treatments.

10. The method of claim 1, wherein said determining a preventative treatment further comprises determining a plurality of preventative treatments, the method further comprising:
 comparing a cost associated with each of said plurality of preventative treatments; and
 selecting at least one of said plurality of preventative treatments based on said comparing.

11. The method of claim 10, wherein said selecting further comprises:
 selecting a preventative treatment having a lowest cost.

12. The method of claim 1, wherein the preventative treatment corresponds to at least one condition.

13. The method of claim 12, further comprising:
 determining a future cost for the at least one condition, wherein the future cost is determined based on a probability of the customer contracting the condition.

14. The method of claim 12, further comprising:
 determining a future cost for the at least one condition, wherein the future cost is determined based on a probability of the customer contracting the condition within a predetermined time.

15. The method of claim 12, further comprising:
 determining a future cost, wherein the future cost is determined based on total cost for treating the condition.

16. The method of claim 1, further comprising:
 receiving a confirmation from a third party that the preventative treatment has been adopted by the customer.

17. The method of claim 16, further comprising:
 updating profile information for the customer based on the confirmation.

18. The method of claim 1, wherein the benefit is provided by an insurer of the customer.

19. The method of claim 18, wherein the benefit is determined based on a probability that the customer will remain insured by the insurer for a predetermined time.

20. The method of claim 1, further comprising:
 receiving a security for the benefit from the customer.

21. The method of claim 20, wherein the security comprises an authorization to charge a financial account in the amount of the benefit.

22. The method of claim 21, wherein the financial account comprises at least one of: a checking account, a savings account, a credit card account, and an alternative currency account.

23. The method of claim 20, wherein the security is used to reimburse the payment of the benefit when a predetermined condition is not met.

24. The method of claim 23, wherein the predetermined condition comprises a determination that the preventative treatment was adopted.

25. The method of claim 23, wherein the predetermined condition comprises a determination that the preventative treatment was adopted within a predetermined time.

26. The method of claim 23, wherein the predetermined condition comprises a requirement that the customer remain insured by an insurer for a predetermined time.

27. The method of claim 23, wherein the predetermined condition comprises a requirement that the customer selects an insurance provider.

28. The method of claim 1, further comprising:
 assigning a treatment provider for the selected preventative treatment.

29. The method of claim 1, wherein the benefit comprises at least one of: a currency amount, an alternate currency amount, a percentage discount on a purchase, and a reduced insurance premium.

30. The method of claim 1, in which providing the benefit comprises receiving a confirmation that the preventative treatment has been adopted.

31. The method of claim 1, wherein the benefit is provided to a third party involved in a transaction with the customer.

32. The method of claim 1, further comprising:
determining the benefit based on an expected future cost.

33. The method of claim 1, further comprising:
determining a present value of a future cost associated with the preventative treatment; and
determining the benefit based on the present value.

34. The method of claim 1, wherein the benefit is provided in at least one installment payment.

35. The method of claim 1, wherein the benefit is provided to one of: a party referring the customer and a party identified by the customer.

36. The method of claim 1, wherein the benefit is provided by at least one of: an insurer, a group of insurers, a physician, an employer, a family member of the customer, a government agency, a drug manufacturer, a medical equipment manufacturer, an automobile repair center and a maintenance provider.

37. The method of claim 1, further comprising:
receiving a medical statistic of the customer with the identification.

38. The method of claim 1, wherein the identification does not include a name of the customer.

39. The method of claim 1, wherein the preventative treatment comprises an agreement to avoid the undertaking of a hazardous activity.

40. The method of claim 1, wherein the preventative treatment comprises an educational assignment regarding a condition.

41. The method of claim 40, wherein the educational assignment comprises at least one of: attendance of an educational seminar and reading educational literature.

42. The method of claim 1, wherein said determining a preventative treatment further comprises determining a preventative treatment based on profile information corresponding to the customer.

43. The method of claim 1,
wherein the third party is a third party merchant; and
wherein offering the benefit to the customer toward the transaction if the customer adopts the preventative treatment comprises:
after receiving the identification of the customer involved in the transaction with the third party merchant, offering the benefit to the customer toward the transaction between the customer and the third party merchant if the customer adopts the preventative treatment.

44. The method of claim 1,
wherein the third party is a third party merchant; and
wherein offering the benefit to the customer toward the transaction if the customer adopts the preventative treatment comprises:
in response to receiving the identification of the customer involved in the transaction with the third party merchant, offering the benefit to the customer toward the transaction between the customer and the third party merchant if the customer adopts the preventative treatment.

45. An apparatus for providing a benefit to a customer, comprising:
a processor; and
a memory in operative communication with the processor, the memory including a plurality of processing instructions for directing the processor to:
receive an identification of a customer involved in a transaction,
wherein the identification comprises at least one of: an identifier associated with the customer and a name of the customer;
identify a preventative treatment for the customer;
offer a benefit to the customer toward the transaction if the customer adopts the preventative treatment;
receive an indication that the customer agrees to adopt the preventative treatment; and
provide the benefit.

46. A computer-readable medium encoded with processing instructions for implementing a method, performed by a computer, for providing a benefit to a customer, the method comprising:
receiving an identification of a customer involved in a transaction,
wherein the identification comprises at least one of: an identifier associated with the customer and a name of the customer;
identifying a preventative treatment for the customer; and
offering a benefit to the customer toward the transaction if the customer adopts the preventative treatment;
receiving an indication that the customer agrees to adopt the preventative treatment; and
providing the benefit.

47. A method for providing a benefit, comprising:
receiving, by a controller comprising at least one processor, a first identification of a transaction involving a customer,
wherein the first identification comprises at least one of: an identifier associated with the customer and a name of the customer;
transmitting, by the controller, a second identification of a preventative treatment to be adopted by the customer;
receiving, by the controller, an indication that the preventative treatment has been adopted by the customer; and
providing, via the controller, a benefit to the customer toward the transaction.

48. The method of claim 47, wherein the receiving further comprises receiving the identification from at least one of: the customer, a merchant, a web site operator, an acquaintance of the customer, a family member related to the customer, a doctor, a pharmacist, an insurance provider, and a government agency.

49. The method of claim 47, wherein said transaction comprises at least one of: a purchase of a product, a purchase of a service, an insurance premium, and an online purchase.

50. The method of claim 47, wherein the profile information comprises at least one of:
an age of the customer, a gender of the customer, a geographic location corresponding to a residence of the customer, a medical history of the customer, a medical history of the customer's family, an occupation of the customer, a previous preventative treatment adopted by the customer, and at least one preventative treatment not adopted by the customer.

51. The method of claim 47, wherein the preventative treatment further comprises at least one of:
a preventative health treatment, a preventative automobile repair, and a preventative home maintenance repair.

52. The method of claim 51, wherein the preventative health treatment comprises at least one of:
a blood pressure screening, a teeth-cleaning treatment, a mammogram, a pap smear, a sigmoidoscopy, a colonoscopy, an immunization, a psychiatric examination, a psychological examination, a dental examination and a physical examination.

53. The method of claim 47, wherein said determining a preventative treatment further comprises:
determining the preventative treatment based on a list of preventative treatments not undertaken by the customer.

54. The method of claim 47, wherein said determining a preventative treatment further comprises:
determining the preventative treatment based on a list of preventative treatments not undertaken by the customer within a predetermined time.

55. The method of claim 47, wherein said determining a preventative treatment further comprises:
determining a plurality of preventative treatments, wherein the customer may adopt at least one of said plurality of preventative treatments.

56. The method of claim 47, wherein said determining a preventative treatment further comprises determining a plurality of preventative treatments, the method further comprising:
comparing a future cost associated with each of said plurality of preventative treatments; and
selecting at least one of said plurality of preventative treatments based on said comparing.

57. The method of claim 56, wherein said selecting further comprises:
selecting a preventative treatment having at least one of: a lowest cost and a highest savings.

58. The method of claim 56, wherein the preventative treatment corresponds to at least one condition.

59. The method of claim 58, wherein the future cost is determined based on a probability of the customer contracting the condition.

60. The method of claim 58, wherein the future cost is determined based on a probability of the customer contracting the condition within a predetermined time.

61. The method of claim 58, wherein the future cost is determined based on a total cost for treating the condition.

62. The method of claim 47, wherein said adopting comprises an agreement by the customer to undertake the preventative treatment.

63. The method of claim 47, further comprising:
receiving a confirmation from a third party that the preventative treatment has been adopted by the customer.

64. The method of claim 63, further comprising:
updating profile information corresponding to the customer based on the confirmation.

65. The method of claim 47, wherein the benefit is provided by an insurer of the customer.

66. The method of claim 65, further comprising:
determining a future cost based on a probability that the customer will remain insured by the insurer for a predetermined time; and
selecting a preventative treatment based on the future cost.

67. The method of claim 47, further comprising:
receiving a security for the benefit from the customer.

68. The method of claim 67, wherein the security comprises an authorization to charge a financial account in the amount of the benefit.

69. The method of claim 68, wherein the financial account comprises at least one of: a checking account, a savings account, a credit card account, and an alternative currency account.

70. The method of claim 67, wherein the security is used to reimburse the payment of the benefit when a predetermined condition is not met.

71. The method of claim 70, wherein the predetermined condition comprises a determination that the preventative treatment was adopted.

72. The method of claim 70, wherein the predetermined condition comprises a determination that the preventative treatment was adopted within a predetermined time.

73. The method of claim 70, wherein the predetermined condition comprises a requirement that the customer remain insured by an insurer for a predetermined time.

74. The method of claim 70, wherein the predetermined condition comprises a requirement that the customer selects an insurance provider.

75. The method of claim 47, further comprising:
assigning a treatment provider for the selected preventative treatment.

76. The method of claim 47, wherein the benefit comprises at least one of: a currency amount, an alternate currency amount, a percentage discount on a purchase, and a reduced insurance premium.

77. The method of claim 47, wherein the benefit is provided to the customer.

78. The method of claim 47, wherein the benefit is provided to the customer after receipt of a confirmation that the preventative treatment has been adopted.

79. The method of claim 47, wherein the benefit is provided to a third party involved in the transaction.

80. The method of claim 47, further comprising:
determining the benefit based on an expected future cost.

81. The method of claim 47, further comprising:
determining an expected present value of a future cost; and
determining the benefit based on the present value.

82. The method of claim 47, wherein the benefit is provided in at least one installment payment.

83. The method of claim 47, wherein the benefit is provided to at least one of: a party referring the customer, and a party identified by the customer.

84. The method of claim 47, wherein the benefit is provided by at least one of: an insurer, a group of insurers, a physician, an employer, a family member of the customer, a government agency, a drug manufacturer, a medical equipment manufacturer, an automobile repair center and a maintenance provider.

85. The method of claim 47, further comprising:
receiving a medical statistic of the customer with the identification.

86. The method of claim 47, wherein the identification does not include a name of the customer.

87. The method of claim 47, wherein the preventative treatment comprises an agreement to avoid the undertaking of a hazardous activity.

88. The method of claim 47, wherein the preventative treatment comprises an educational assignment regarding a condition.

89. The method of claim 88, wherein the educational assignment comprises at least one of: attendance of an educational seminar and reading educational literature.

90. The method of claim 47, wherein said determining a preventative treatment further comprises determining a preventative treatment based on profile information corresponding to the customer.

91. A computer readable medium encoded with processing instructions for implementing a method for providing a benefit, the method comprising:
- receiving, by a controller comprising at least one processor, a first identification of a transaction involving a customer,
  - wherein the first identification comprises at least one of: an identifier associated with the customer and a name of the customer;
- transmitting, by the controller, a second identification of a preventative treatment to the customer;
- receiving, by the controller, an indication that the preventative treatment has been adopted by the customer; and
- providing, via the controller, a benefit to the customer toward the transaction.

92. An apparatus for providing a benefit, comprising:
- a processor; and
- a memory in operative communication with the processor, the memory for storing a plurality of processing instructions directing the processor to:
- receive a first identification of a transaction involving a customer,
  - wherein the first identification comprises at least one of: an identifier associated with the customer and a name of the customer;
- transmit a second identification of a preventative treatment to the customer;
- receive an indication that the preventative treatment has been adopted by the customer; and
- provide a benefit to the customer toward the transaction.

93. A method for providing a benefit, comprising:
- receiving, by a controller comprising at least one processor, a first identification of a transaction between a customer and a third party;
- determining, by the controller, a preventative treatment and a benefit;
- transmitting, by the controller, a second identification of the preventative treatment and a third identification of the benefit to the customer;
- receiving, by the controller, an indication that the preventative treatment has been adopted by the customer; and
- providing the benefit toward the transaction between the customer and the third party in response to said indication.

94. The method of claim 93, wherein a value for the benefit is determined from an expected future cost corresponding to the preventative treatment.

95. A method for providing a benefit to a customer, comprising:
- receiving, by a controller comprising at least one processor and associated with at least one insurer, an identification of a customer involved in a transaction with a third party merchant, the transaction being via a web site of the third party merchant;
- after receiving the identification of the customer involved in the transaction with the third party merchant,
  - selecting, by the controller comprising at least one processor and associated with the at least one insurer, a preventative treatment for the customer;
- after receiving the identification of the customer involved in the transaction with the third party merchant,
  - offering, by the controller comprising at least one processor and associated with the at least one insurer, a benefit to the customer toward the transaction between the customer and the third party merchant in exchange for the customer agreeing to adopt the preventative treatment;
- receiving, by the controller comprising at least one processor and associated with the at least one insurer, an indication that the customer agrees to adopt the preventative treatment; and
- providing the benefit toward the transaction between the customer and the third party merchant.

96. A computer readable medium encoded with processing instructions for implementing a method for providing a benefit, the method comprising:
- receiving, by a controller comprising at least one processor, a first identification of a transaction between a customer and a third party;
- determining, by the controller, a preventative treatment and a benefit;
- transmitting, by the controller, a second identification of the preventative treatment and a third identification of the benefit to the customer;
- receiving, by the controller, an indication that the preventative treatment has been adopted by the customer; and
- providing the benefit toward the transaction between the customer and the third party in response to said indication.

97. An apparatus for providing a benefit, comprising:
- a processor; and
- a memory in operative communication with the processor, the memory for storing a plurality of processing instructions directing the processor to:
- receive a first identification of a transaction between a customer and a third party;
- determine a preventative treatment and a benefit;
- transmit a second identification of the preventative treatment and a third identification of the benefit to the customer;
- receive an indication that the preventative treatment has been adopted by the customer; and
- provide the benefit toward the transaction between the customer and the third party in response to said indication.

* * * * *